United States Patent [19]

Hill

[11] Patent Number: 4,803,985
[45] Date of Patent: Feb. 14, 1989

[54] GASTROPLASTY METHOD

[76] Inventor: Carl W. Hill, 1360 6th St., Suite 370, San Pedro, Calif. 90732

[21] Appl. No.: 830,288

[22] Filed: Feb. 14, 1986

[51] Int. Cl.⁴ .............................................. A61B 17/00
[52] U.S. Cl. .................................................... 128/346
[58] Field of Search ................................ 128/346, 1 R

[56] References Cited

U.S. PATENT DOCUMENTS

| | | | |
|---|---|---|---|
| 4,246,893 | 1/1981 | Berson | 128/346 X |
| 4,458,681 | 7/1984 | Hopkins | 128/346 |
| 4,586,501 | 5/1986 | Claracq | 128/346 X |

FOREIGN PATENT DOCUMENTS 3421567 12/1985 Fed. Rep. of Germany ...... 128/346

Primary Examiner—Michael H. Thaler
Attorney, Agent, or Firm—Benjamin DeWitt

[57] ABSTRACT

In a procedure for control of obesity, a clamp is placed across the stomach in a manner to partition the stomach into proximal and distal chambers with a restricted flow passage therebetween. An adjustable volume member is carried by the clamp and is coupled to distally positioned means for adjusting the dimensions of said member thereby controlling the effective cross-sectional area of said flow passage.

2 Claims, 1 Drawing Sheet

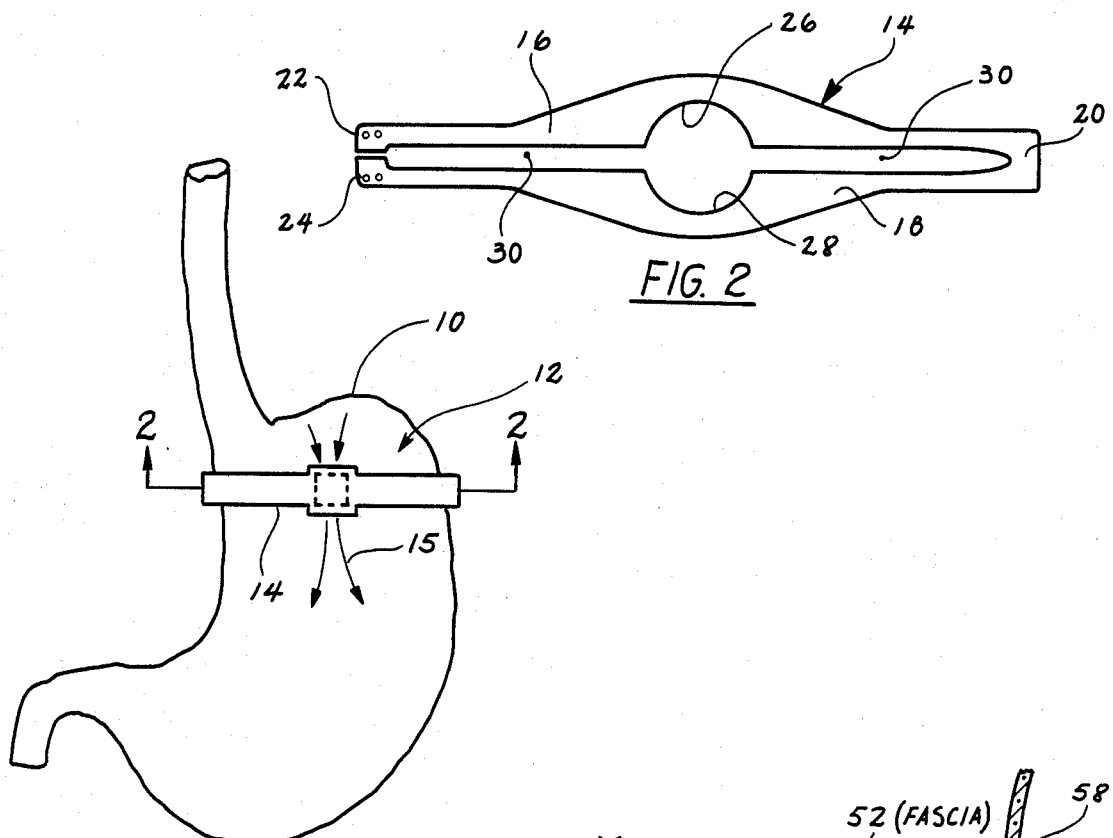
FIG. 2
FIG. 1
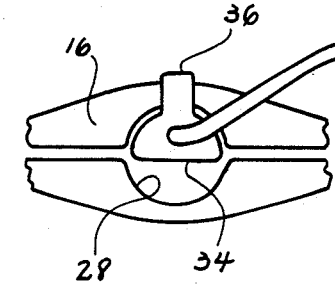
FIG. 3
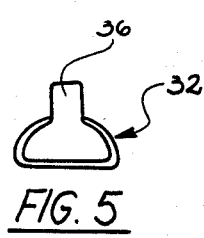
FIG. 5
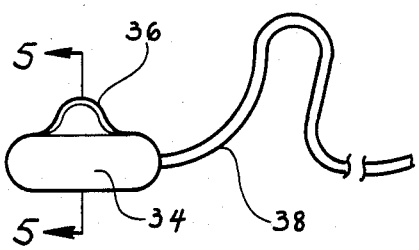
FIG. 4

GASTROPLASTY METHOD

BACKGROUND OF THE INVENTION

The present invention relates generally to treatment of severe obesity in humans, and more particularly to an improved surgical procedure, and apparatus used in such procedure, for treating severe obesity that is not readily controlled by diet, medication, or behavior modification techniques.

Extreme obesity is a major disease both in the United States and other countries. Its complications include hypertension, diabetes, coronary artery disease, stroke, congestive heart failure, venous disease, orthopedic problems and pulmonary insufficiency. Attempts to reduce extreme obesity by dietary, and/or behavior modification techniques hve been generally quite unsuccessful. Diets simply do not work. Drug therapy and psychotherapy are effective only as long as the patient is under intensive treatment; any loss of weight is usually quickly regained after the patient discontinues the treatment. In general, non-surgical techniques have had a long-term success rate of less than 2%. Heretofore, several surgical techniques have been developed aimed at a reduction of absorption of nutrients from ingested food. Of these, the procedure that has been performed on the greatest number of patients as a surgical attempt to control morbid obesity is the jejunoileal bypass. The disadvantage of the jejunoileal bypass is its long-term consequences. An unacceptably large fraction of bypass patients experience severe and debilitating complications such as progressive liver failure, electrolyte imbalance, renal disease and/or bowel disorders.

In *Contemporary Surgery,* volume 23, December 1983, Griffen et al. describe several surgical procedures that avoid the metabolic distrubances commonly associated with the jejunoileal bypass. These surgical techniques generally involve stapling together the two walls of the stomach to provide a reduced-volume proximal pouch for receiving ingested food. These stapling techniques necessarily involve multiple perforations of the stomach wall with a substantial risk of leakage, tearing and infection. Moreover, the cross-sectional area of the thru-flow aperture, left open after the stapling operation, cannot be predetermined or controlled with any reasonable accuracy. Depending on the metabolism of the particular patient, the resulting absorption of nutrients may be far off the mark. In addition, rows of metallic staples are difficult to remove; these stapling operations cannot be reversed without extreme risk to the patient.

In short, none of the surgical procedures used heretofore have been completely satisfactory. A need exists for an improved method and apparatus for gastroplastic treatment of morbid obesity.

Accordingly, it is an object of my invention to enable gastric partitioning with reduced risk of post-operative leakage and/or infection while providing for post-surgical adjustment of the flow to distal portions of the gastrointestinal tract, thereby enhancing post-operative control of obesity.

It is a further object of my invention to enable gastroplasty with no invasion of the gastrointestinal tract while providing for adjustment, from time to time, of the rate of permitted flow from the proximal portion of the stomach to distal portions of the gastrointestinal system.

It is a still further object of my invention to provide a gastroplasty method and apparatus that features post-operative adjustment of the flow of nutrients to the intestinal tract while enabling rapid and facile installation with reduced risk of gastric leakage and infection.

SUMMARY OF THE INVENTION

My invention provides a method of, and an apparatus for, obesity control in which the stomach is partitioned into proximal and distal chambers with a restricted flow passageway extending from the former to the latter. The apparatus includes distally-positioned control means for adjusting the effective cross section of this passageway. After recuperation from the surgical procedure, the patient's weight-loss rate may be monitored on an outpatient basis; and the permitted flow of nutrients from the proximal chamber to the distal pouch, and thence to the intestinal tract, may be adjusted from time to time as appropriate to regulate and stabilize the patient's weight regardless of the particular patient's metabolism. The apparatus employed in practicing my invention includes a clamping device having two arms separated sufficiently to permit positioning of the two arms contiguously adjacent opposite side walls of the stomach, thereby allowing co-apting of the two walls of the stomach without crushing the tissue. This stomach clamp is preferably formed of a rigid or semi-rigid polymer, such as high density polyethylene. The two arms are integrally joined together at one end, while being separable at the other end, sufficiently to permit sliding the stomach clamp across a normal stomach at a position intermediate the proximal and distal openings of the stomach. Approximately mid-way between its ends, at least one of the arms is provided with a substantially semi-cylindrical aperture or pressure relief region. When the clamp is properly positioned on the stomach, this aperture permits the two walls of the stomach to separate slightly, adjacent the pressure relief aperture of the stomach clamp, thereby forming a small diameter flow passageway extending from the proximal chamber to the lower, distal chamber. This allows passage of food from the proximal chamber into the distal chamber and, hence, to the intestinal tract.

Attached to the interior of the clamp's central aperture is an expandable balloon, formed of a physiologically compatible polymer. This balloon is preferably secured to one arm of the stomach clamp by means of a sling that passes around the arm substantially at the position of the pressure-relief portion. A fluid conduit, connected to communicate with the interior of the balloon, extends from the balloon to a distally positioned fluid reservoir, preferably located in the subcutaneous fatty layer outside the muscle wall of the abdomen and at a location chosen for convenient access on an outpatient basis. Preferably, this fluid reservoir is provided with an anterior surface, formed of latex rubber coated with a tissue-compatible polymer, and suitable for injection of supplementary fluid into the reservoir, by means of a hypodermic needle pushed through the skin and the anterior wall of the fluid reservoir. The fluid reservoir is relatively non-expansible; therefore, injection of fluid into this reservoir causes flow through the connecting fluid conduit to the control balloon, positioned exteriorly adjacent to the stomach wall at the location of the thru-flow passageway from the proximal chamber to the distal chamber. Expansion of the fluid-filled balloon decreases the effective cross section of the inter-chamber flow passageway, thereby effecting an adjustment of the rate at which food is allowed to pass into the distal chamber.

Methods and apparatus in accordance with my invention have several advantages over stapled gastroplasty and gastric bypass procedures: my invention is non-invasive, that is no penetration of the wall of the stomach is involved; therefore, there is less risk of infection and/or leakage. Control of obesity in accordance with my invention is readily reversible, by removing the stomach clamp. Most importantly, my invention enables post-operative adjustment and control of the patient's obesity not heretofore obtained in any other procedure or apparatus. The permitted rate of flow of food from the proximal chamber to the distal chamber can be adjusted from time to time on an outpatient basis with substantially no risk to the patient.

The foregoing features and other objects and advantages of my invention will be more fully understood from a consideration of the following specification of a preferred implementation taken with the accompanying drawings, wherein similar reference characters refer to similar parts.

BRIEF DESCRIPTION OF THE DRAWINGS

FIG. 1 is an anterior-posterior plan view of a proximal gastric partitioning in accordance with a preferred implementation of my invention;

FIG. 2 is a cross-sectional view of the stomach clamping device taken along the lines 2—2 of FIG. 1;

FIG. 3 illustrates, partially in section, the apparatus of my invention implanted within a human, including post-surgical adjustment on an outpatient basis;

FIG. 4 illustrates on a larger scale a portion of the assembly shown in FIG. 3; and FIG. 5 is a cross-sectional view taken along lines 5—5 of FIG. 4.

DETAILED DESCRIPTION OF A PREFERRED EMBODIMENT

Referring now more particularly to the drawings, the several figures illustrate a presently preferred implementation of my gastroplasty procedure and apparatus for treating obesity that is ot controllable by diet or medication. As best shown in FIGS. 1 and 2, a stomach clamp 14 having first and second arms 16 and 18, extends across a stomach 10 to partition the stomach into a proximal chamber or pouch 12 and a distal chamber or pouch 13. The clamp 14 is preferably located at a position such that the proximal chamber has a volume of about 30 to 40 cubic centimeters. The two arms 16 and 18 of the clamp are integrally joined at one end 20; at the other end they are readily separable and ar provided with apertures 22 and 24 extending normal to the plane of FIG. 2. The clamp is passed across the upper stomach and the open ends pressed into opposition and secured together with ligatures passing through the holes 22 and 24. Between the arms 16 and 18 the clamp is provided with an elongated slot 30 so that the two arms are separated sufficiently to co-apt the two walls of the stomach but without significant trauma or crushing of the stomach wall tissue. Approximately midway between its ends the two arms of the clamp define semi-cylindrical apertures or pressure relief portions 26 and 28, so that when the clamp is properly positioned on the stomach, a substantially cylindrical passageway is provided from the proximal chamber 12 to the distal chamber 13. Positioned in the aperture 26 of clamp arm 16 is a balloon-like element 34 secured to the arm 16 by a sling 36 that passes around the mid portion of the arm 16. Preferably, this sling 36 is formed integrally with the balloon, 34, and is sufficiently elastomeric so that the sling may be passed over the arm 16 at its open end and pushed along the arm to the aperture 26. Balloon-like member 34 is preferably formed of a physiologically-compatible elastomeric polymer such as silicone rubber or latex rubber exteriorly coated with silicone elastomer. As best shown in FIGS. 4 and 5, balloon 34 is generally cylindrical in shape with a somewhat flattened lower surface. Alternatively, if the apertures 26 and 28 are substantially cup shaped, the balloon 34 may take the form of an oblate spheroid, i.e., a substantially football-shaped balloon.

Extending from one end of the balloon 34, and communicating with the interior thereof is a fluid conduit 38 adapted for introducing or removing fluid from the balloon 34 to thereby adjust its dimensions. During the surgical procedure, fluid conduit 38 is extended from the region of the stomach to the anterior of the abdomen at a location below the rib cage and convenient for hypodermic needle access on an outpatient basis. As shown in FIG. 3, conduit 38 extends outwardly through the peritoneum 51 and muscle wall 54 to a suitable location within the subcutaneous fatty layer 58 of the abdominal wall. At its outer end, conduit 38 is connected to a hollow fluid reservoir 40, preferably formed of a tissue-compatible elastomer such as silicone rubber. This reservoir 40, which is preferably about 3 to 4 centimeters in diameter and about 1½ to 2 centimeters thick, is positioned in the fatty layer 58 between fascia 52 and the skin. Polymeric tabs 42 and 44 are securd by suturing to the underlying fascia 52.

After the patient has recovered from the gastroplasty procedure, the patient is seen periodically on an outpatient basis, to consider whether the patient is losing weight at an appropriate rate while receiving sufficient nutrients to avoid metabolic distrubances. This of course depends on the metabolism of the specific patient and the effective crosssectional area of the flow passage from the proximal pouch 12 to the distal pouch 13. Flow of food through this passage is indicated by reference numeral 15 in FIG. 1. If during such outpatient treatment it is found that the particular patient, perhaps having a lower than normal metabolism, is not losing weight at an appropriate rate, then a hypodermic needle and syringe 56 is used to penetrate the reservoir 40 for introducing supplementary fluid into the reservoir and by way of conduit 38 into balloon 34. This injection of hydraulic fluid expands the circumference of ballon 34 so that its interior surface presses more vigorously against the adjacent stomach wall and reduces the effective cross-sectional area of the flow passageway between the stomach walls through apertures 26 and 28. Reservoir 40, filling tube 38 and balloon 34 are preferably filled with a tissue-compatible liquid such as physiological saline solution or silicone oil. Reservoir 40 preferably has have relatively thick walls as compared to those of balloon 34 so that when supplementary fluid is hypodermically injected into reservoir 40, the fluid does not expand reservoir 40, but rather, flows through conduit 38 to expand balloon 34.

While a preferred implementation of my gastroplasty procedure and apparatus has been described in detail, it is to be understood that such is intended by way of example only and that various modifications and permutations may be made therein. It is intended, therefore, that the following claims be deemed to encompass all such modifications and permutations as fall within the true spirit and scope of my invention.

What I claim is:

1. In a method of gastric partitioning for obesity control, the steps of;
   (a) placing a clamp havig two arms, at least one of which includes a pressure-relief portion, across a stomach with said two arms disposed, respectively, adjacent opposite exterior surfaces of the stomach;
   (b) partially closing the interspace between said arms so as to partition said stomach into two chambers with said pressure-relief portion of the clamp defining a flow passage between said chambers;
   (c) providing an adjustable-volume member between one of said arms and the exterior surface of the stomach; and
   (d) providing distally-positioned means for adjusting the dimensions of said member and thereby controlling the effective cross-sectional area of said flow passage.

2. A method in accordance with claim 1 wherein said dimensions-adjusting means comprises fluid reservoir coupled for fluid communication with said member and wherein, subsequent to steps (a), (b), (c) and (d) fluid is caused to flow between said reservoir and said member for expanding the latter and decreasing the effective cross sectional area of the flow passage.

* * * * *